United States Patent
Hashimoto et al.

(10) Patent No.: US 10,661,142 B2
(45) Date of Patent: May 26, 2020

(54) MOVEMENT ANALYSIS DEVICE FOR DETERMINING WHETHER A TIME RANGE BETWEEN A START TIME AND A COMPLETION TIME OF A PREDETERMINED MOVEMENT BY A TARGET PERSON IS VALID, AND MOVEMENT ANALYSIS METHOD AND RECORDING MEDIUM

(71) Applicants: CASIO COMPUTER CO., LTD., Shibuya-ku, Tokyo (JP); NARA INSTITUTE OF SCIENCE AND TECHNOLOGY, Ikoma-shi, Nara (JP)

(72) Inventors: Shogo Hashimoto, Tokyo (JP); Ryo Okumura, Tokyo (JP); Yutaka Arakawa, Nara (JP); Hirohiko Suwa, Osaka (JP); Yuta Takahashi, Nara (JP); Chishu Amenomori, Kyoto (JP)

(73) Assignees: CASIO COMPUTER CO., LTD., Tokyo (JP); NARA INSTITUTE OF SCIENCE AND TECHNOLOGY, Nara (JP)

( * ) Notice: Subject to any disclaimer, the term of this patent is extended or adjusted under 35 U.S.C. 154(b) by 128 days.

(21) Appl. No.: 15/813,541

(22) Filed: Nov. 15, 2017

(65) Prior Publication Data
US 2018/0140925 A1 May 24, 2018

(30) Foreign Application Priority Data
Nov. 21, 2016 (JP) .................. 2016-226234

(51) Int. Cl.
| | |
|---|---|
| A61B 5/11 | (2006.01) |
| A63B 71/06 | (2006.01) |
| G06K 9/00 | (2006.01) |
| A63B 69/36 | (2006.01) |

(52) U.S. Cl.
CPC ........ *A63B 69/3608* (2013.01); *A61B 5/1116* (2013.01); *A61B 5/1121* (2013.01);
(Continued)

(58) Field of Classification Search
None
See application file for complete search history.

(56) References Cited

U.S. PATENT DOCUMENTS

| | | | |
|---|---|---|---|
| 9,162,130 B2 | 10/2015 | Shibuya | |
| 2011/0230273 A1* | 9/2011 | Niegowski | ........... A43B 3/0005 473/199 |

(Continued)

FOREIGN PATENT DOCUMENTS

| | | |
|---|---|---|
| CN | 102814034 A | 12/2012 |
| JP | 2008054977 A | 3/2008 |

(Continued)

OTHER PUBLICATIONS

Chinese Office Action dated Apr. 24, 2019 (and English translation thereof) issued in Chinese Application No. 201711162053.3.
(Continued)

*Primary Examiner* — Idowu O Osifade
(74) *Attorney, Agent, or Firm* — Holtz, Holtz & Volek PC

(57) ABSTRACT

A movement analysis device includes a sensor information acquisition unit and a swing identification processing unit. The sensor information acquisition unit acquires sensor information that is movement information from a sensor unit which is attached to a target person and which senses the movement of the target person. The swing identification processing unit individually identifies the time of the start of the movement and the time of the completion thereof with reference to a predetermined threshold value in a predetermined timing of the sensor information that is the movement information acquired from the sensor information acquisi-
(Continued)

tion unit. The swing identification processing unit identifies a movement within the range of the operation based on the time of the start of the movement and the time of the completion that are identified.

11 Claims, 9 Drawing Sheets

(52) U.S. Cl.
CPC ...... *A63B 71/0619* (2013.01); *A63B 71/0686* (2013.01); *G06K 9/00342* (2013.01); *A61B 5/1123* (2013.01); *A61B 2503/10* (2013.01); *A61B 2562/0219* (2013.01); *A63B 2208/0204* (2013.01); *A63B 2220/34* (2013.01); *A63B 2220/44* (2013.01); *A63B 2220/803* (2013.01)

(56) References Cited

U.S. PATENT DOCUMENTS

| | | | | |
|---|---|---|---|---|
| 2014/0180632 | A1* | 6/2014 | Yataka | A61B 5/1126 702/153 |
| 2014/0295982 | A1 | 10/2014 | Shibuya | |
| 2016/0089568 | A1 | 3/2016 | Shibuya | |
| 2017/0215771 | A1 | 8/2017 | Sayo et al. | |
| 2018/0336797 | A1* | 11/2018 | Bergh | G09B 19/0038 |

FOREIGN PATENT DOCUMENTS

| | | |
|---|---|---|
| JP | 2014121456 A | 7/2014 |
| JP | 2015178026 A | 10/2015 |
| JP | 2016022308 A | 2/2016 |
| JP | 2016036681 A | 3/2016 |
| JP | 2016067410 A | 5/2016 |

OTHER PUBLICATIONS

Japanese Office Action dated Oct. 8, 2019 (and English translation thereof) issued in Japanese Patent Application No. 2016-226234.
Japanese Office Action (and English translation thereof) dated Apr. 7, 2020 issued in Japanese Patent Applicaton No. 2016-226237.

\* cited by examiner

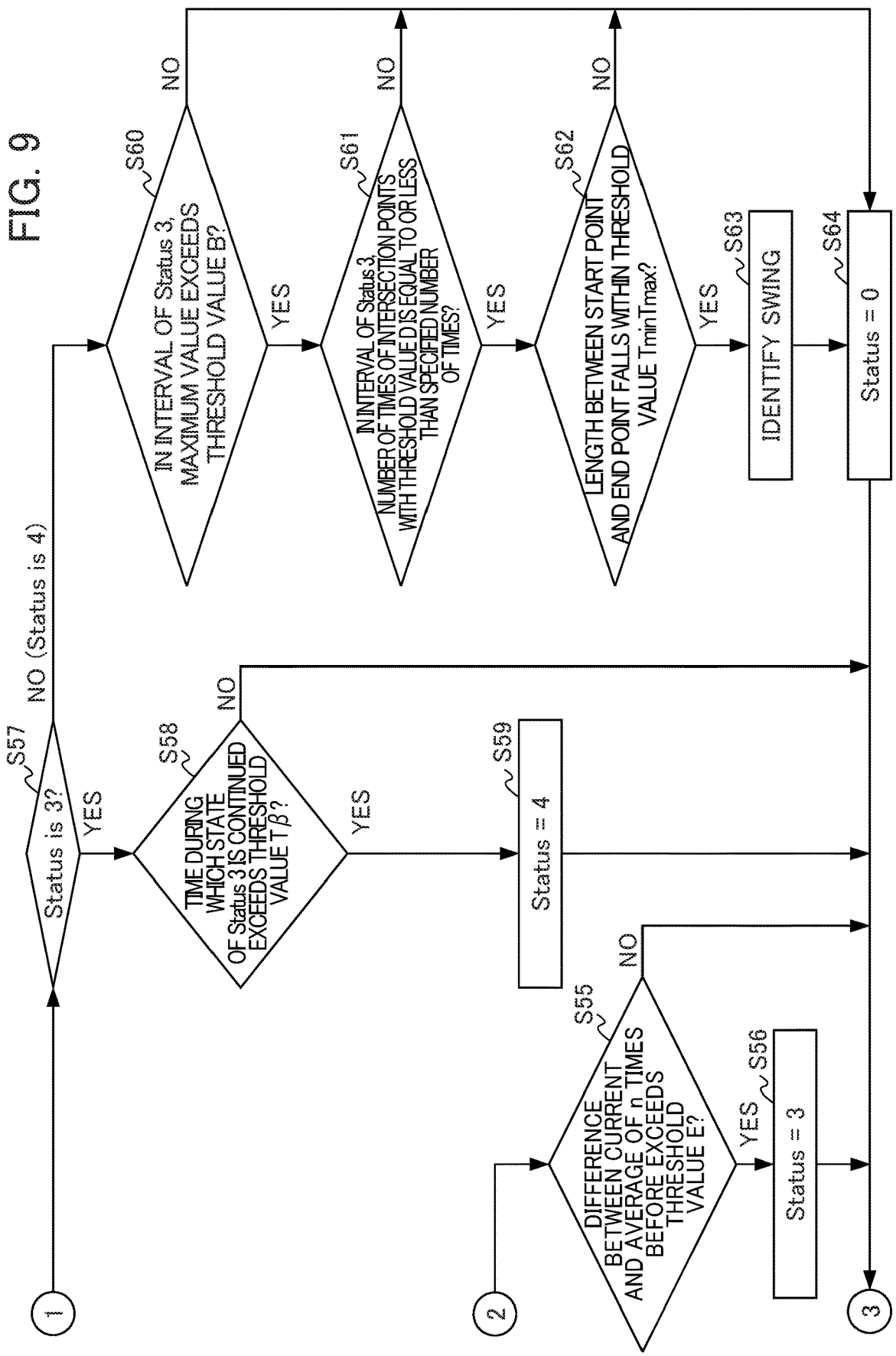

MOVEMENT ANALYSIS DEVICE FOR DETERMINING WHETHER A TIME RANGE BETWEEN A START TIME AND A COMPLETION TIME OF A PREDETERMINED MOVEMENT BY A TARGET PERSON IS VALID, AND MOVEMENT ANALYSIS METHOD AND RECORDING MEDIUM

CROSS-REFERENCE TO RELATED APPLICATIONS

This application is based upon and claims the benefit of priority under 35 USC 119 of Japanese Patent Application No. 2016-226234 filed on Nov. 21, 2016 the entire disclosure of which, including the description, claims, drawings, and abstract, is incorporated herein by reference in its entirety.

BACKGROUND OF THE INVENTION

Field of the Invention

The present invention relates to a movement analysis device, a movement analysis method and a recording medium.

Related Art

Conventionally, as disclosed in Japanese Unexamined Patent Application Publication No. 2015-178026, there has been a technology that detects an impact in the golf swing data of a user and identifies the range of the swing movement by the target person by using the point of the detected impact as the basis.

SUMMARY OF THE INVENTION

A movement analysis device according to one aspect of the present invention comprising: a processor, wherein the processor performs: acquisition processing in which movement information is acquired from a sensor device that is attached to a target person and that senses a series of movements by the target person; and first identification processing in which based on the movement information acquired by the acquisition processing and a predetermined threshold value, a time of start of the movement and a time of completion thereof are identified. A movement analysis method according to one aspect of the present invention is performed in a movement analysis device, the movement analysis method comprising: acquisition processing of acquiring movement information from a sensor device which is attached to a target person and which senses a series of movements of the target person; and identification processing of identifying a time of start of the movement and a time of completion thereof based on the movement information acquired by the acquisition processing and a predetermined threshold value. A non-transitory recording medium according to one aspect of the present invention which stores a computer-readable program for controlling a movement analysis device, wherein the program makes a processor perform: acquisition processing in which movement information is acquired from a sensor device that is attached to a target person and that senses a series of movements of the target person; and identification processing in which based on the movement information acquired by the acquisition processing and a predetermined threshold value, a time of start of the movement and a time of completion thereof are identified.

BRIEF DESCRIPTION OF THE DRAWINGS

FIG. 9 is a flowchart illustrating another flow of the swing identification processing performed by the movement analysis device 2 in FIG. 3 having the functional configuration shown in FIG. 5.

DETAILED DESCRIPTION OF THE INVENTION

Embodiments of the present invention will be described below with reference to the drawings.

First Embodiment

Figure 1:
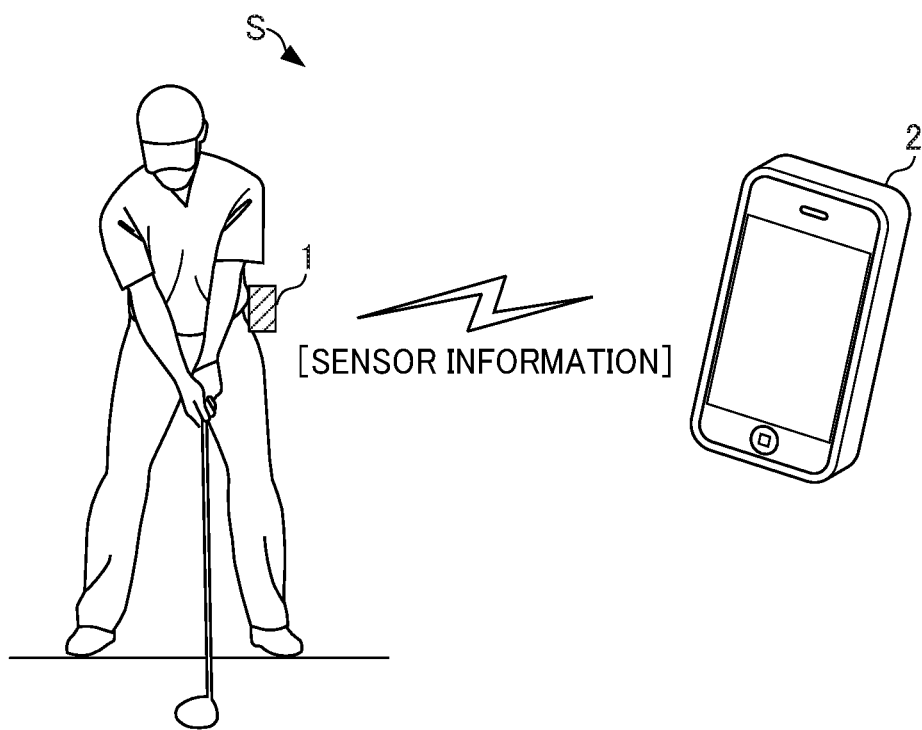
FIG. 1 is a system configuration diagram showing the system configuration of a movement analysis system S according to an embodiment of the present invention.

FIG. 1 is a system configuration diagram showing the system configuration of a movement analysis system S according to an embodiment of the present invention. The movement analysis system. S includes, as shown in FIG. 1, a sensor unit 1 and a movement analysis device 2.

The sensor unit 1 has at least a sensing function for sensing the movements of a fitting target and a communication function for transmitting sensed data (hereinafter referred to as "sensor information") to the movement analysis device 2. In the present embodiment, the sensor unit 1 is fitted around the waist of a person who performs a golf swing, and a series of movements in the swing are sensed as the movement of the fitting target.

The movement analysis device 2 has at least a communication function for receiving the sensor information transmitted from the sensor unit 1 and an analysis function for analyzing the sensor information so as to identify the series of movements and each individual movement in the series of movements. In the present embodiment, the movement analysis device 2 identifies, by analysis, the series of movements in the swing and the individual movements that form the swing such as an address, a take-back, a downswing, a follow and a finish.

Figure 2:
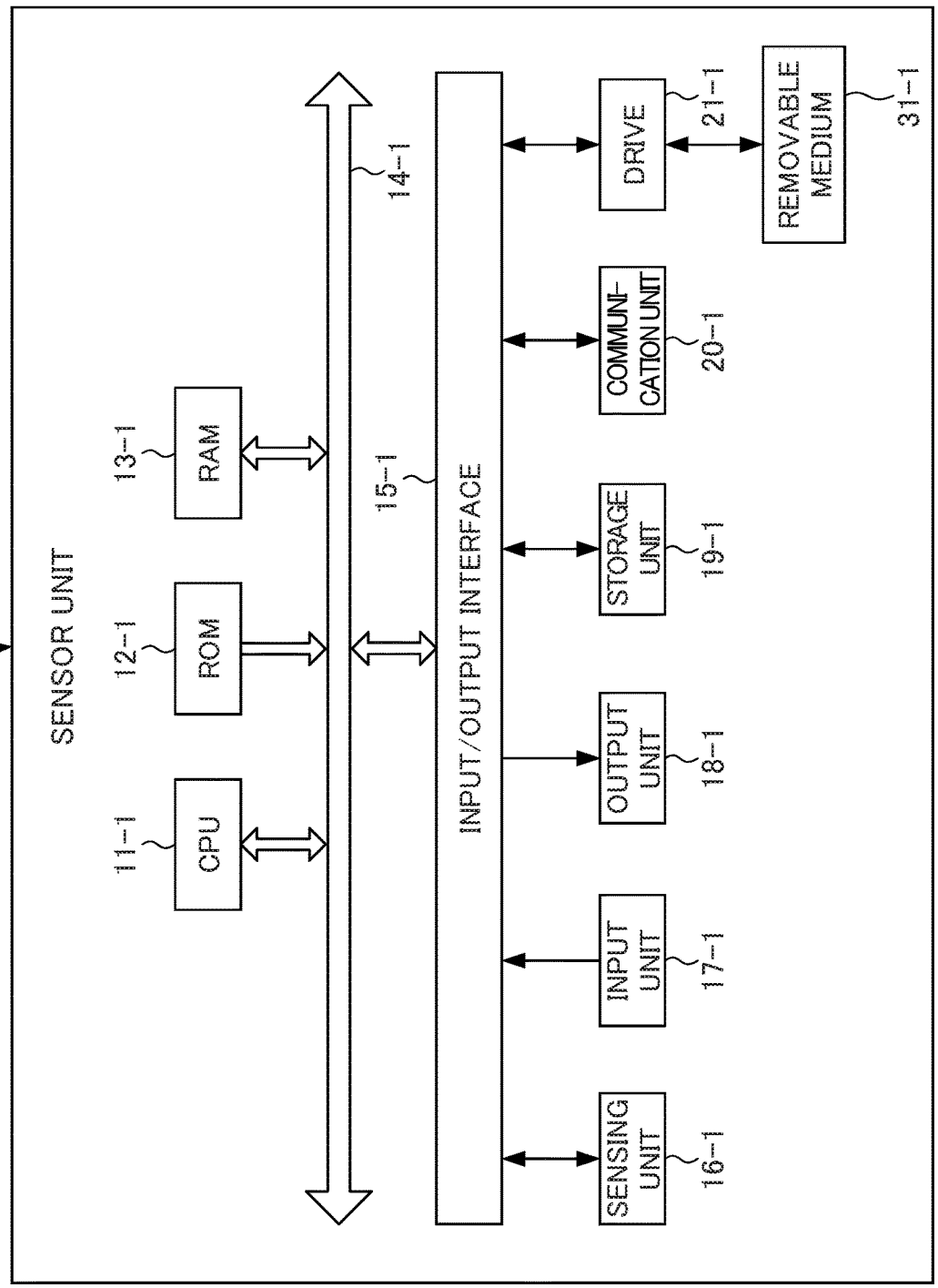
FIG. 2 is a block diagram showing the hardware configuration of a sensor unit 1 according to an embodiment of the present invention.

FIG. 2 is a block diagram showing the hardware configuration of the sensor unit 1 according to an embodiment of the present invention. The sensor unit 1 includes a central processing unit (CPU) 11-1, a read only memory (ROM) 12-1, a random access memory (PAN) 13-1, a bus 14-1, an input-output interface 15-1, a sensing unit 16-1, an input unit 17-1, an output unit 18-1, a storage unit 19-1, a communication unit 20-1, and a drive 21-1.

The CPU 11-1 executes various types of processing according to a program stored in the ROM 12-1 or a program loaded from the storage unit 19-1 into the RAM 13-1.

Data, etc. required upon the CPU 11-1 executing the various processing is stored in the RAM 13-1 as appropriate.

The CPU 11-1, ROM 12-1 and RAM 13-1 are connected to each other via the bus 14-1. In addition, the input/output interface 15-1 is also connected to this bus 14-1. The input-output interface 15-1 is further connected to the sensing unit 16-1, the input unit 17-1, the output unit 18-1, the storage unit 19-1, the communication unit 20-1, and the drive 21-1.

The sensing unit 16-1 is formed with various types of sensors such as a gyro sensor and a three-axis angular velocity sensor and detects at least an angular velocity generated in the sensor unit 1 according to the movement of a user so as to output it as the sensor information. In the present embodiment, a sampling rate is set to 200 Hz.

The input unit 17-1 is configured by various buttons and the like, and inputs a variety of information in accordance with instruction operations by the user. The output unit 18-1 is configured by the display unit, a speaker, and the like, and outputs images and sound. The storage unit 19-1 is configured by DRAM (Dynamic Random Access Memory) or the like, and stores data of various images. The communication unit 21-1 controls communication with a different apparatus (not shown in the drawings) via a network including the Internet.

A removable medium 31-1 composed of a magnetic disk, an optical disk, a magneto-optical disk, semiconductor memory or the like is installed in the drive 21-1, as appropriate. Programs that are read via the drive 21-1 from the removable medium 31-1 are installed in the storage unit 19-1, as necessary. Similarly to the storage unit 19-1, the removable medium 31-1 can also store a variety of data such as the image data stored in the storage unit 21-1.

Figure 3:
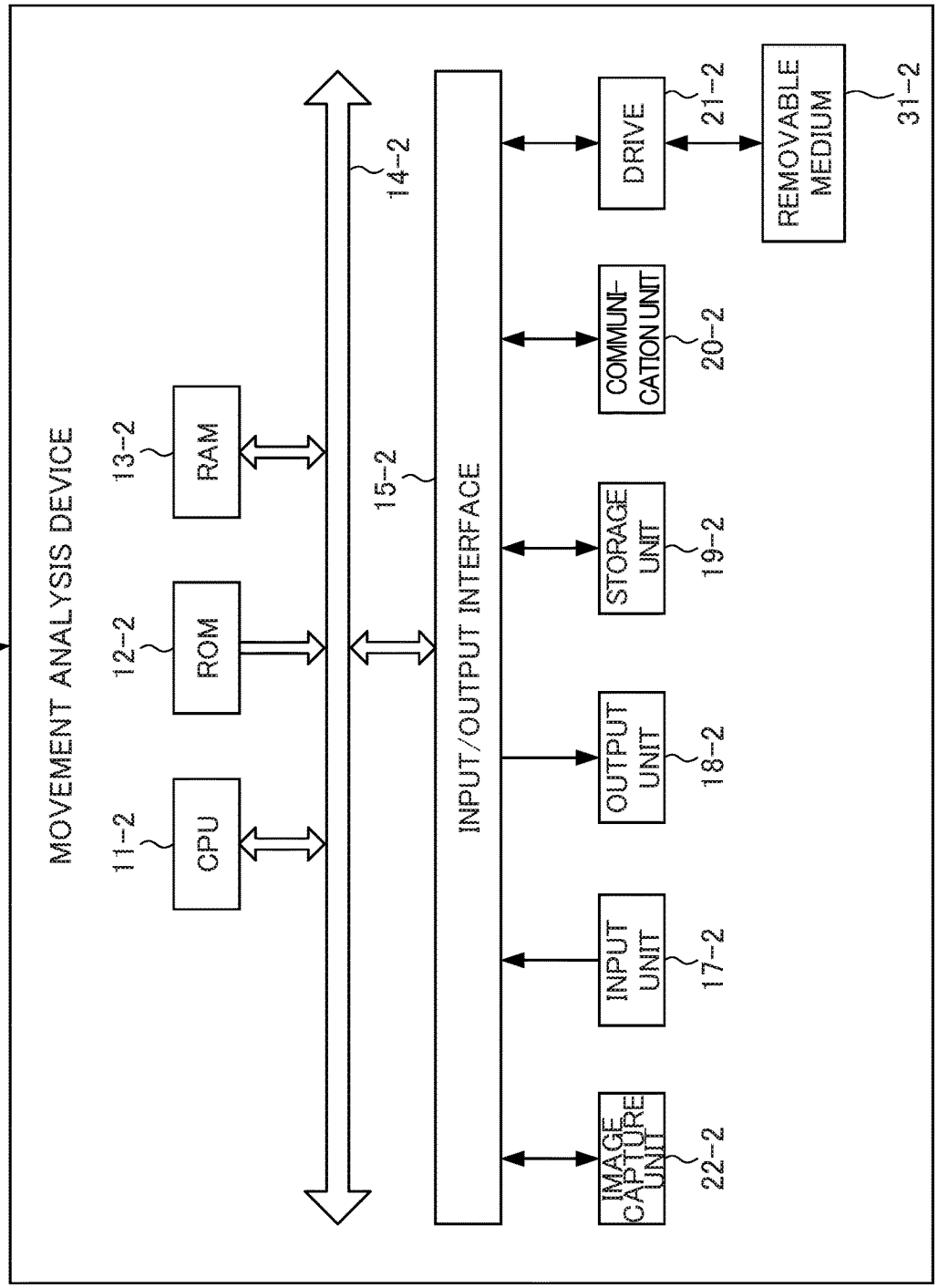
FIG. 3 is a block diagram showing the hardware configuration of a movement analysis device 2 according to an embodiment of the present invention.

FIG. 3 is a block diagram showing the hardware configuration of the movement analysis device 2 according to an embodiment of the present invention. The movement analysis device 2 is configured as, for example, an information device such as a smartphone.

The movement analysis device 2 includes a. CPU 11-2, a ROM 12-2, a RAM 13-2, a bus 14-2, an input-output interface 15-2, an input unit 17-2, an output unit 18-2, a storage unit 19-2, a communication unit 20-2, a drive 21-2 and an image capture unit 22-2. In other words, the sensor unit 1 and the movement analysis device 2 are the same as each other in the configuration of the CPU 11-1 to the drive 21-1 and the configuration of the CPU 11-2 to the drive 21-2, excluding the sensing unit 16-1. In the movement analysis device 2, the description of the same configuration as in the sensor unit 1 will be omitted.

In addition to the CPU 11-2 to the drive 21-2, the movement analysis device 2 further includes the image capture unit 22-2.

The image capture unit 22-2 includes an optical lens unit and an image sensor, which are not shown.

In order to photograph a subject, the optical lens unit is configured by a lens such as a focus lens and a zoom lens for condensing light. The focus lens is a lens for forming an image of a subject on the light receiving surface of the image sensor. The zoom lens is a lens that causes the focal length to freely change in a certain range. The image capture unit 22-2 also includes peripheral circuits to adjust setting parameters such as focus, exposure, white balance, and the like, as necessary.

The image sensor is configured by an optoelectronic conversion device, an AFE (Analog Front End), and the like. The optoelectronic conversion device is configured by a CMOS (Complementary Metal Oxide Semiconductor) type of optoelectronic conversion device and the like, for example. Light incident through the optical lens unit forms an image of a subject in the optoelectronic conversion device. The optoelectronic conversion device optoelectronically converts (i.e. captures) the image of the subject, accumulates the resultant image signal for a predetermined time interval, and sequentially supplies the image signal as an analog signal to the AFE. The AFE executes a variety of signal processing such as A/D (Analog/Digital) conversion processing of the analog signal. The variety of signal processing generates a digital signal that is output as an output signal from the image capture unit 22-2. Such an output signal of the image capture unit 22-2 is hereinafter referred to as "data of a captured image". Data of a captured image is supplied to the CPU 11-2, an image processing unit (not illustrated), and the like as appropriate.

The movement analysis device 2 configured as described above has the function of being able to use various threshold values for the sensor information acquired from the sensor unit 1 so as to easily identify swing portions in golf.

In the movement analysis device 2, a [stationary state] (Status 0) is first identified from the sensor information (in the present embodiment), a state [movement start state] (Status 1) where a backswing is started is identified from the identified stationary state, a series of movements which appear to be a swing is identified from a series of movements including the identified stationary state as a swing [swing candidate] (Status 2) and whether the swing candidate applies to a swing [swing] (Status 3) is finally identified. In other words, in the movement analysis device 2, under the four Statuses of the [stationary state], the [movement start state], the [swing candidate] and the [swing], threshold values (in the present embodiment, threshold values A to D which are relatively different threshold values) corresponding to the individual Statuses are used, and thus the swing is identified.

Figure 4:
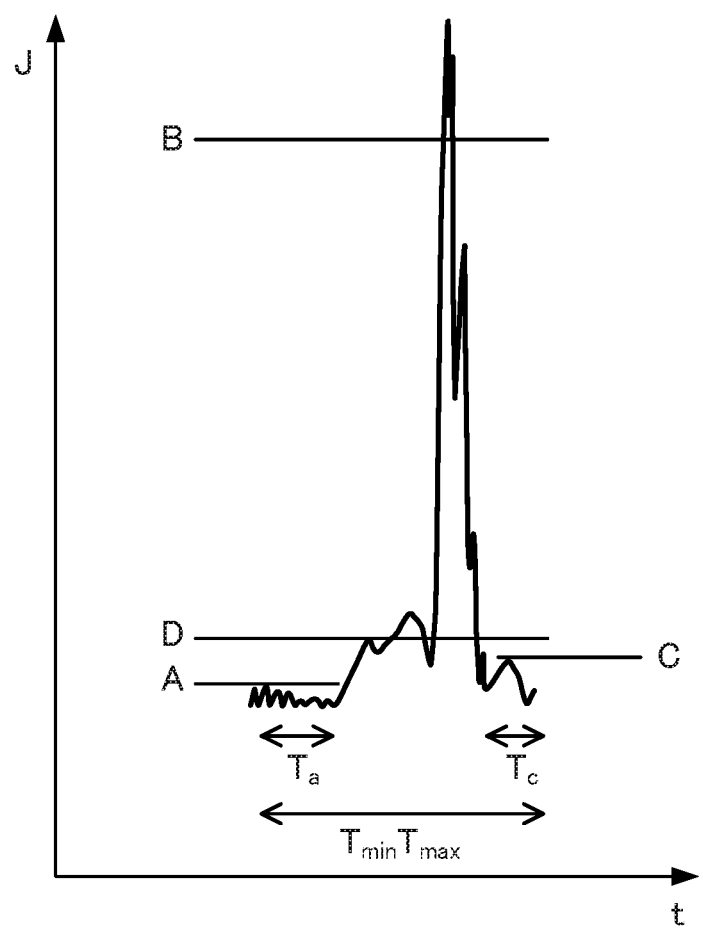
FIG. 4 is a schematic diagram for illustrating a method of identifying a swing in the present embodiment.

FIG. 4 is a schematic diagram for illustrating a method of identifying the swing in the present, embodiment. In order for the swing to be identified, first, in the acquired sensor information, the values of the individual angular velocities of an X axis, a Y axis, and a Z axis are combined, and thus a combined gyro value is calculated. The combined gyro value J is calculated by use of formula (I) below.

$$J=\sqrt{x^2+y^2+z^2} \qquad (1)$$

"x" is the value of the angular velocity of the X axis, "y" is the value of the angular velocity of the Y axis and "z" is the value of the angular velocity of the Z axis.

In the present embodiment, as shown in FIG. 4, from a graph where the calculated combined gyro values J are arranged chronologically so as to be varied with time, the threshold values corresponding to the Statuses 0 to 3 and the combined gyro values J are compared with each other, with the result that the swing portions are identified.

[Identification of Stationary State] (Status 0)

In this Status, from the graph where the combined gyro value J is changed chronologically, the address state of the swing is detected. In the present embodiment, when the stationary state is continued for a predetermined amount of time, it is assumed that it is highly likely that the address state of the swing is produced, and thus the stationary state which is continued for a certain period is identified. For example, a state where the combined gyro value J continuously falls below a threshold value A: a threshold value (intensity) for determining the stationary state for a threshold value Ta: a threshold value (time) for determining the stationary state or more is detected as the stationary state. In order to identify the stationary state, the threshold value A is first used and is the lowest value among the individual threshold values. The threshold value Ta is a value representing the time necessary for an average golf player to perform the address.

[Identification of Movement Start] (Status 1)

In this Status, from the graph where the combined gyro value J is changed chronologically, the time at which the backswing is started in the address state of the swing is detected. In the present embodiment, if after the change from the Status 0 to the Status 1, the threshold value for detecting the stationary state is exceeded, it is assumed that it is highly likely that the backswing is started in the stationary state, and thus the time at which the threshold value for detecting the stationary state was exceeded is identified. In the identification of the start of the movement, a state where, for example, the combined gyro value J exceeds the threshold value A: the threshold value (intensity) for determining the stationary state is detected as the time at which the movement of the backswing is started. After the detection processing is performed, a change to the Status 2 is performed.

[Identification as swing candidate] (Status 2)

In this Status, the time of completion of the swing corresponding to the time of start of the backswing detected in the Status 1 is identified, and thus the swing candidate is detected. The swing movement is completed by the finish in which the final stationary state is continued for a certain period through a certain level or more of instantaneous motion (impact movement) after the start of the backswing. In the present embodiment, a state where the combined gyro value J continuously falls below a threshold value C: a threshold value (intensity) for determining the finish which is the stationary state of the final movement through the time of start of the backswing for a threshold value Tc: a threshold value (time) for determining the stationary state or more is detected as the finish in the swing movement. The threshold value C is used at a timing after the threshold value A and is varied depending on the player as compared with the stationary state, with the result that the threshold value C is set higher than the threshold value A. The threshold value Tc is a value representing the time necessary for a general finish, and in the present embodiment, the threshold value Tc is a period that is shorter than the threshold value Ta.

[Identification as Swing] (Status 3)

In this Status, in a state (swing candidate state) where the probability of the swing identified up to the Status 2 is high, the characteristic of the swing is further determined by a threshold value so as to be identified as the present swing.

1) The maximum value in the interval of the Status 2 exceeds a threshold value B: a threshold value (intensity) for identifying the steep value of a downswing and determining it as a swing.
2) A threshold value D: the number of intersection points of a threshold value (the number of times) for preventing noise data from being determined as the swing falls within a specified number in the present embodiment, 5 to 10 times).
3) A period which is identified as the swing candidate falls within a specified amount of time (threshold value TminTmax: a threshold value (time) for determining a time during which the swing is performed, and in the present embodiment, 650 to 3000 frames). When the three conditions described above are satisfied, the movement within the period is identified as the swing. The threshold value B is used in a period between the threshold value A and the threshold value C and is the highest value among the individual threshold values. The threshold value D is used in the period between the threshold value A and the threshold value C and is lower than the threshold value B but higher than the threshold value A and the threshold value C. The threshold value TminTmax is a value for the time necessary from the start of the movement of the swing by an average golf player to the completion of the movement.

Figure 5:
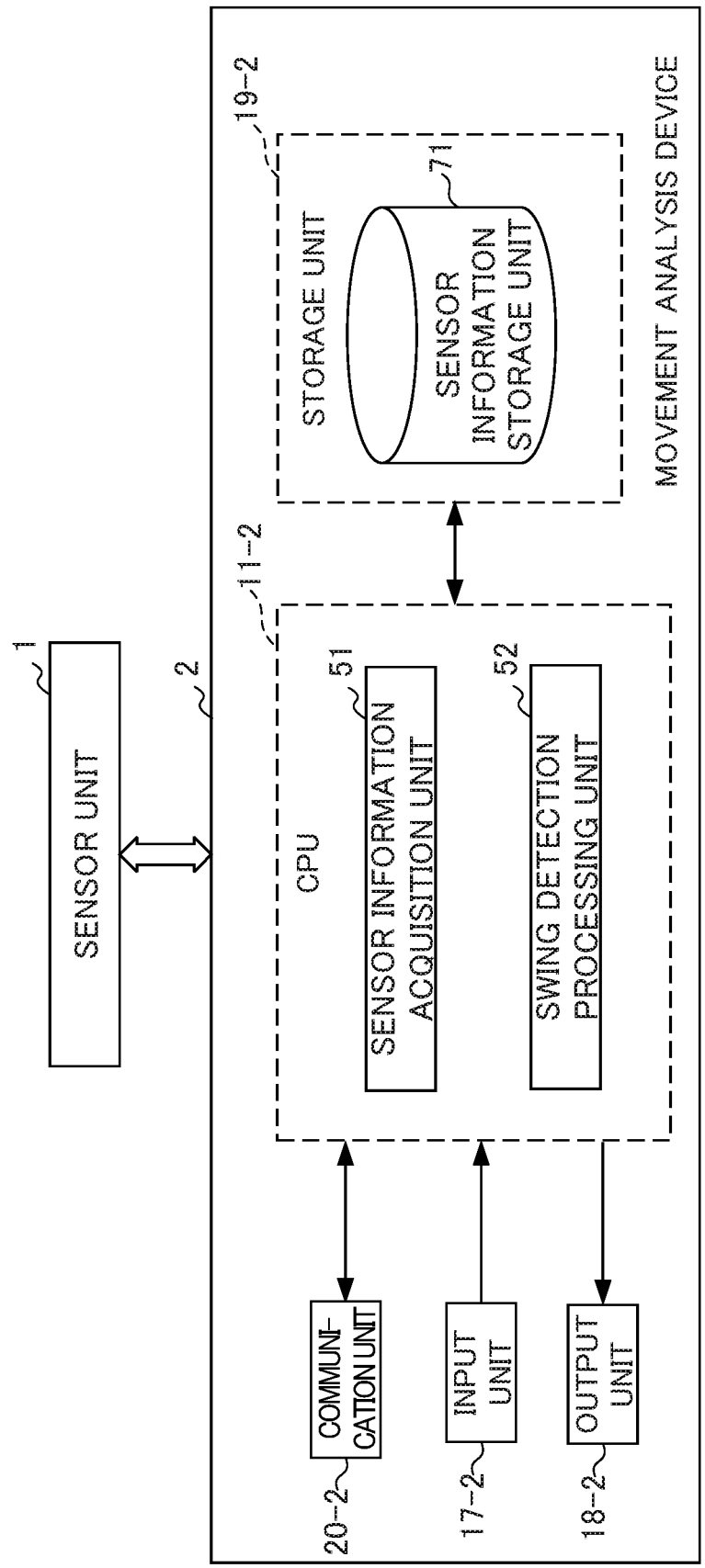
FIG. 5 is a functional block diagram showing a functional configuration for performing swing identification processing in the functional configuration of the movement analysis device 2 in FIG. 3.

FIG. 5 is a functional block diagram showing a functional configuration for performing swing identification processing in the functional configuration of the movement analysis device 2 in FIG. 3. The swing identification processing refers to a series of processing steps in which a swing is detected from movement information acquired from the sensor unit 1.

When the swing identification processing is performed, as shown in FIG. 5, a sensor information acquisition unit 51 and a swing identification processing unit 52 function in the CPU 11-2.

In one region of the storage unit 19-2, a sensor information storage unit 71 set. In the sensor information storage unit 71, the sensor information acquired from the sensor unit 1 is stored.

The sensor information acquisition unit 51 can acquire, for example, the sensor information stored in the sensor information storage unit 71. Specifically, the sensor information acquisition unit 51 acquires, from the sensor information, the combined gyro value J calculated by combining the individual values of the angular velocities of the X axis, the Y axis, and the Z axis by using the formula (1) above.

The swing identification processing unit 52 performs, for example, processing related to the identification of the swing, and can identify, from the acquired sensor information, by use of a predetermined threshold value for each of the Statuses, the time of each of the individual movements forming the swing and the range of the swing itself. Specifically, in addition to the identification of the swing, it is possible to identify, as around the individual movements forming the swing, the address, the start of the backswing, around the time of the finish, and the time of the downswing.

Figure 6:
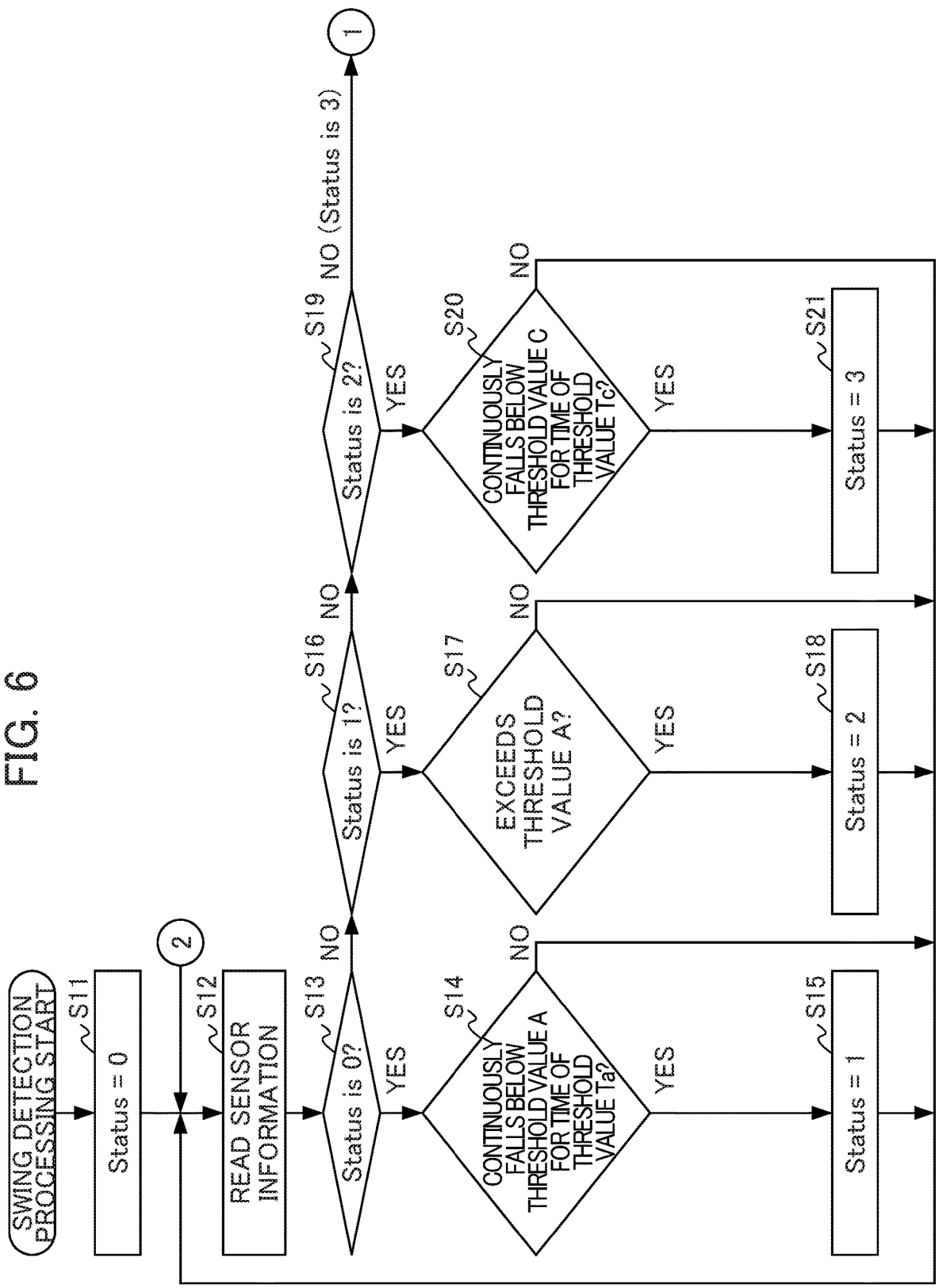
FIG. 6 is a flowchart illustrating the flow of the swing identification processing performed by the movement analysis device 2 in FIG. 3 having the functional configuration shown in FIG. 5.
Figure 7:
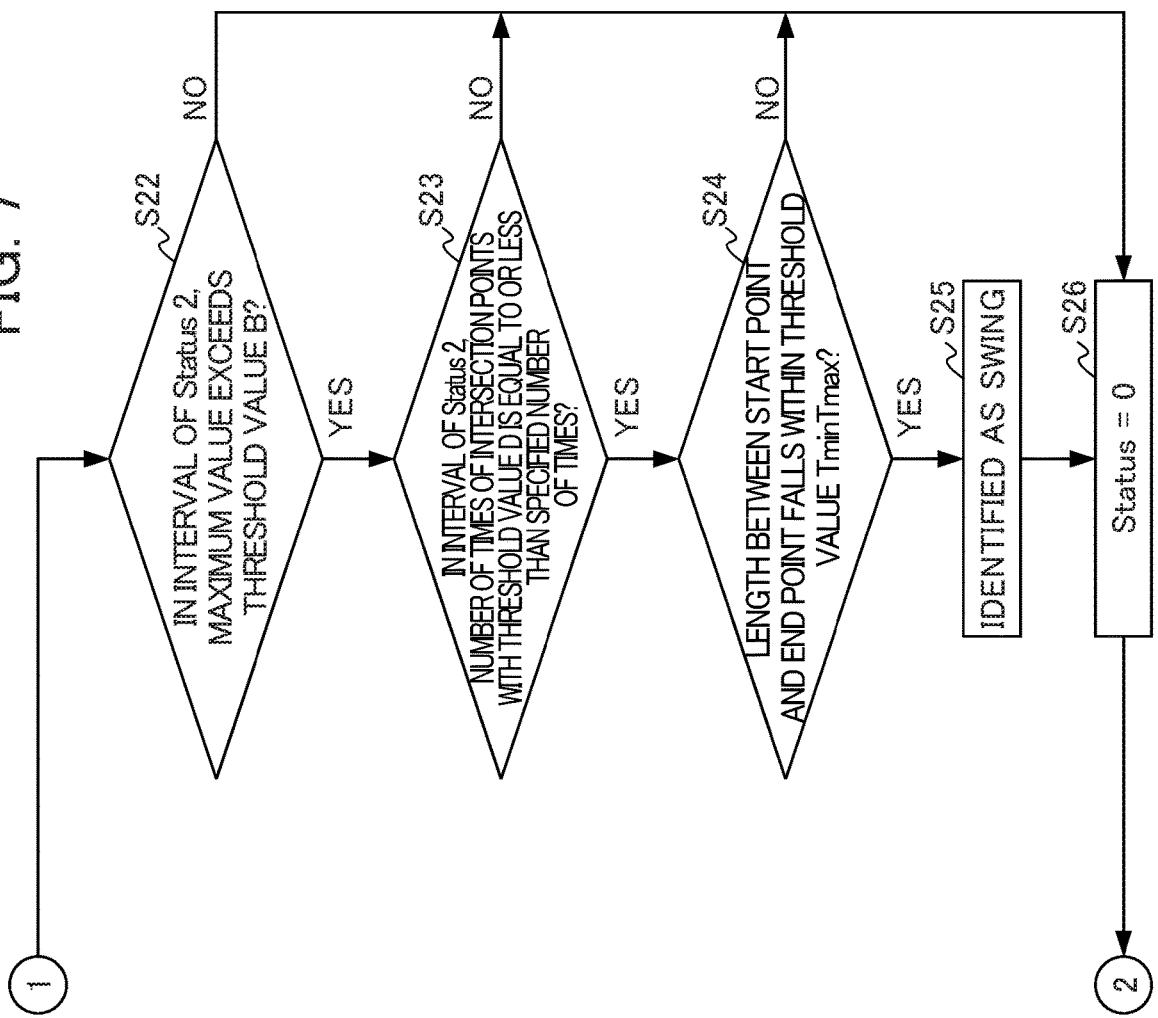
FIG. 7 is a flowchart illustrating the flow of the swing identification processing performed by the movement analysis device 2 in FIG. 3 having the functional configuration shown in FIG. 5.

FIGS. 6 and 7 are flowcharts illustrating the flow of the swing identification processing performed by the movement analysis device 2 in FIG. 3 having the functional configuration shown in FIG. 5. The swing identification processing is started by an operation signaling the start of the swing identification processing performed on the input unit 17-2 by the user. At the start of the swing identification processing, the movement analysis device 2 transmits an instruction to start sensing to the sensor unit 1, and the sensing is started in the sensor unit 1 according to the instruction. In the sensor unit 1, the sensor information obtained by the sensing is sequentially transmitted to the movement analysis device 2. In the movement analysis device 2, the sensor information transmitted from the sensor unit 1 is received and then stored in the sensor information storage unit 71.

In step S11, the swing identification processing unit 52 sets the Status to "0" (in other words, initializes it).

In step S12, the sensor information acquisition unit 51 acquires and reads the sensor information stored in the sensor information storage unit 71.

In step S13, the swing identification processing unit 52 determines whether or not the current Status is "0". When the Status is not "0", in step S13, the determination is NO, and the processing proceeds to step S16. When the Status is "0", in step S13, the determination is YES, and the processing proceeds to step S14.

In step S14, the swing identification processing unit 52 determines whether or not the combined gyro value J continuously falls below the threshold value A for the time of the threshold value Ta. When the combined gyro value J does not continuously fall below the threshold value A for the time of the threshold value Ta, in step S14, the determination is NO, and the processing returns to step S12. When the combined gyro value J continuously falls below the threshold value A for the time of the threshold value Ta, in step S14, the determination is YES, and the processing proceeds to step S15.

In step S15, the swing identification processing unit 52 sets the Status to "1". Thereafter, the processing returns to step S12.

In step S16, the swing identification processing unit 52 determines whether or not the Status is "1". When the Status is not "1", in step S16, the determination is NO, and the processing proceeds to step S19. When the Status is "1", in step S16, the determination is YES, and the processing proceeds to step S17.

In step S17, the swing identification processing unit 52 determines whether or not the combined gyro value J exceeds the threshold value A. When the combined gyro value J does not exceed the threshold value A, in step S18, the determination is NO, and the processing returns to step S12. When the combined gyro value J exceeds the threshold value A, in step S18, the determination is YES, and the processing proceeds to step S18.

In step S18, the swing identification processing unit 52 sets the Status to "2". Thereafter, the processing returns to step S12.

In step S19, the swing identification processing unit 52 determines whether or not the Status is "2". When the Status is not "2", in step S19, the determination is NO, and the processing proceeds to step S22. When the Status is "2", in step S19, the determination is YES, and the processing proceeds to step S20.

In step S20, the swing identification processing unit 52 determines whether or not the combined gyro value J continuously falls below the threshold value C for the time of the threshold value Tc. When the combined gyro value J does not continuously fall below the threshold value C for the time of the threshold value Tc, in step S20, the determination is NO, and the processing returns to step S12. When the combined gyro value J continuously falls below the threshold value C for the time of the threshold value Tc, in step S20, the determination is YES, and the processing proceeds to step S21.

In step S21, the swing identification processing unit 52 sets the Status to "3". Thereafter, the processing returns to step S12.

In step S22, the swing identification processing unit 52 determines whether or not in the interval of the Status 2, the maximum value of the combined gyro value J exceeds the threshold value B. When in the interval of the Status 2, the maximum value of the combined gyro value J does not exceed the threshold value B, in step S22, the determination is NO, and the processing proceeds to step S26. When in the interval of the Status 2, the maximum value of the combined gyro value J exceeds the threshold value B, in step S22, the determination is YES, and the processing proceeds to step S23.

In step S23, the swing identification processing unit 52 determines whether or not in the interval of the Status 2, the intersection points of the combined gyro value J and the threshold value D fall within a range of a specified number of times. When in the interval of the Status 2, the intersection points of the combined gyro value J and the threshold value D do not fall within the range of the specified number of times, in step S23, the determination is NO, and the processing proceeds to step S26. When in the interval of the Status 2, the intersection points of the combined gyro value J and the threshold value D fall within the range of the specified number of times, in step S23, the determination is YES, and the processing proceeds to step S24.

In step S24, the swing identification processing unit 52 determines whether or not a time between the start point of a state where the combined gyro value J continuously falls below the threshold value A for a predetermined time (the threshold value Ta) and the end point of a state where the combined gyro value J continuously falls below the threshold value C for a predetermined time (the threshold value Tc) falls within a predetermined time (the threshold value TminTmax) In other words, whether or not the length from the start point to the end point falls within the threshold value TminTmax is determined. When the length from the start point to the end point does not fail within the threshold value TminTmax, in step S24, the determination is NO, and the processing proceeds to step S26. When the length from the start point to the end point fails within the threshold value TminTmax, in step S24, the determination is YES, and the processing proceeds to step S25.

In step S25, the swing identification processing unit 52 identifies the movement between the start point (Tmin) and the end point (Tmax) as the swing.

In step S26, the swing identification processing unit 52 sets the Status to "0". Thereafter, the processing returns to step S12.

The processing is performed as described above, and thus in the swing movement by the player, it is possible to identify the range of the swing without reference to the time of the impact, and it is also possible to identify the range of the swing by the comparison processing between the combined gyro value J and the individual threshold values, which is light calculation processing.

Second Embodiment

In the present embodiment, unlike the first embodiment described above, when the downswing is identified without detection of the finish, the range of the swing is identified with reference to the time of the downswing. Hence, more accurate address detection processing, the detection processing of the downswing, timeout processing when the downswing cannot be detected and weight processing when the downswing can be detected are added. In other words, in the present embodiment, the timeout processing and the weight processing when the downswing can be detected are added, and thus the number of Statuses is increased. Specifically, the Status 0 is the identification of the stationary state, the Status 1 is the identification of the start of the movement, the Status 2 is the detection of the downswing and the timeout processing, the Status 3 is the weight processing when the downswing can be detected and the Status 4 is the identification processing of the present swing.

Figure 8:
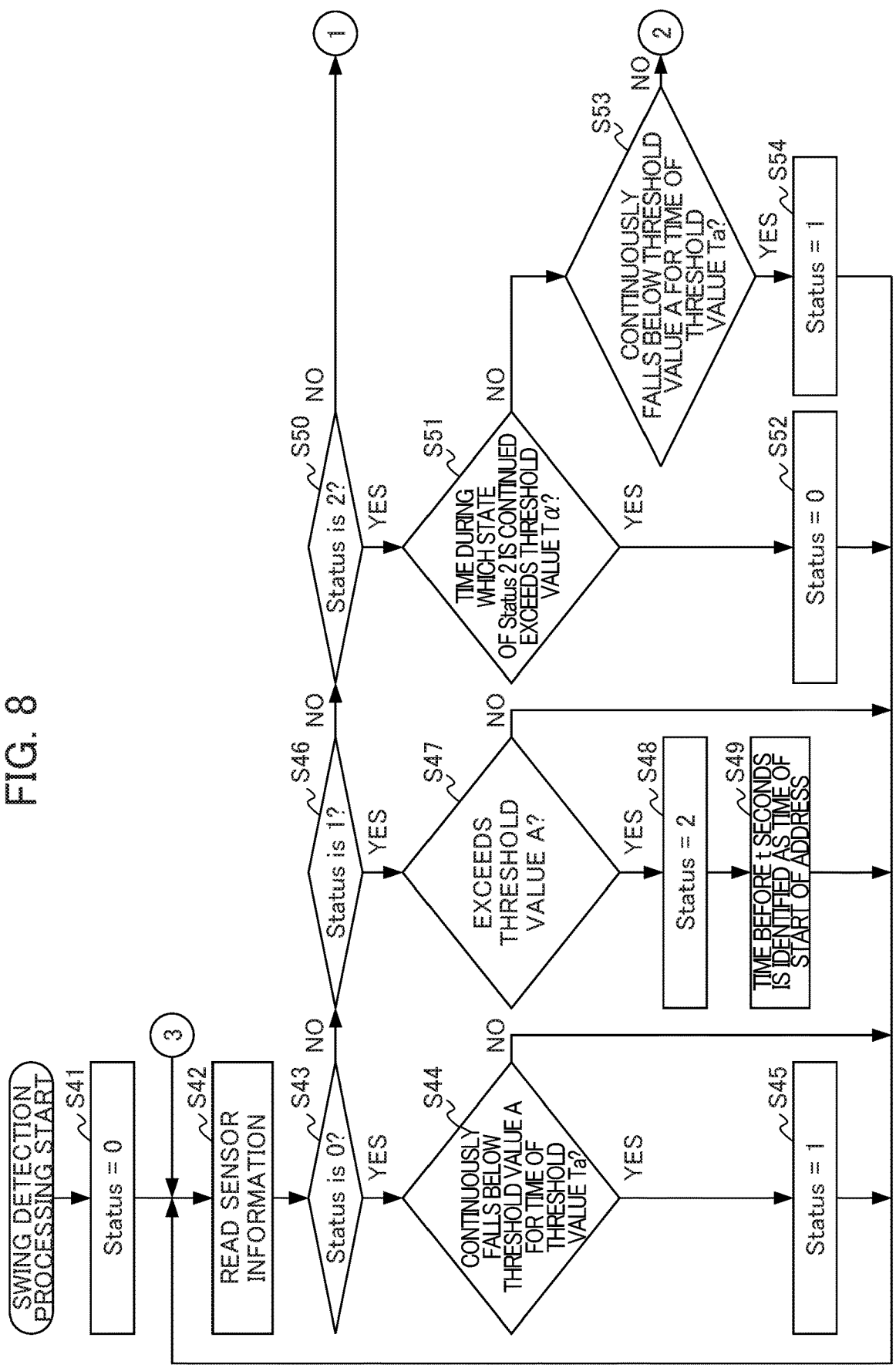
FIG. 8 is a flowchart illustrating another flow of the swing identification processing performed by the movement analysis device 2 in FIG. 3 having the functional configuration shown in FIG. 5.

FIGS. 8 and 9 are flowcharts illustrating the flow of the swing identification processing performed by the movement analysis device 2 in FIG. 3 having the functional configuration shown in FIG. 5. Since in steps S41 to S49, the same processing as in the first embodiment is performed below, the additional flow parts will be described in detail with reference to FIGS. 8 and 9.

[Movement Start Identification and Address Detection Processing]

In step S47, the swing identification processing unit 52 determines whether or not the current combined gyro value J exceeds the threshold value A for determining the stationary state so as to identify the start of the movement. When the threshold value A is not exceeded, in step S47, the determination is NO, and the processing returns to step S42. When the threshold value A is exceeded, in step S47, the determination is YES, and the processing proceeds to step S48.

In step S48, the swing identification processing unit 52 sets the Status to "2". Thereafter, the processing proceeds to step S49.

[Address Identification Processing]

In step S49, the swing identification processing unit 52 identifies the time that is t seconds before the time of the start of the movement as the time of the start of the address from the graph of the combined gyro value J, and thereafter the processing returns to step S42. As the value of t here, value that is arbitrarily set by the user may be used or a fixed value that is previously stored in the storage unit 19-2 may be used.

[Timeout Processing when Downswing Cannot be Detected]

In step S51, the swing identification processing unit 52 determines whether or not the time during which the state of the Status 2 is continued exceeds the time of a threshold value Tα (in the present embodiment, at least a range which does not exceed 3 seconds, 1.5 to 2.5 seconds and 300 to 500 times when it is converted to the number of times the determination processing is performed). When the state of the Status 2 is continued for a predetermined time, in step S51, the determination is YES, and the processing proceeds to step S52. When the state of the Status 2 is not continued for the predetermined time, in step S51, the determination NO, and the processing proceeds to step S53.

In step S52, the swing identification processing unit 52 sets the Status to "0". Thereafter, the processing returns to step S42.

[Waggle Detection Processing]

In step S53, the swing identification processing unit 52 determines whether or not the combined gyro value J continuously falls below the threshold value A for the time of the threshold value Ta. When the combined gyro value J does not continuously fall below the threshold value A for the time of the threshold value Ta, in step S53, the determination is NO, and the processing proceeds to step S55. When the combined gyro value J continuously falls below the threshold value A for the time of the threshold value Ta, in step S53, the determination is YES, and the processing proceeds to step S54.

In step S54, the swing identification processing unit 52 sets the Status to "1". Thereafter, the processing returns to step S42.

[Downswing Detection Processing]

In step S55, the swing identification processing unit 52 determines whether or not a difference between the current combined gyro value J and the average value of the combined gyro values J before a predetermined time (before N times) exceeds a threshold value E. In the present embodiment, the predetermined time is specified to be 10 times, and the threshold value E is set to 0.5. However, there is no limitation to the above values, and the values may be adjusted according to the identification of the swing of each person. When the threshold value E is not exceeded, in step S55, the determination is NO, and the processing returns to step S42. When the threshold value F is exceeded, in step S55, the determination is YES, and the processing proceeds to step S56.

In step S56, the swing identification processing unit 52 sets the Status to "3". Thereafter, the processing returns to step S42.

[Weight Processing when the Downswing Can Be Detected]

In step S58, the swing identification processing unit 52 determines whether or not the time during which the state of the Status 3 is continued exceeds the time of a threshold value Tβ (in the present embodiment, at least a range which does not exceed 3.0 seconds, 1.5 to 2.5 seconds and 400 to 500 times when it is converted to the number of times the determination processing is performed). When the time during which the state of the Status 3 is continued does not exceed the time of the threshold value Tβ, in step S58, the determination is NO, and the processing returns to step S42. When the time during which the state of the Status 3 is continued exceeds the time of the threshold value Tβ, in step S59, the determination is YES, and the processing proceeds to step S59. Thereafter, the swing identification processing unit 52 sets the Status to "4".

In step S59, the swing identification processing unit 52 sets the Status to "4". Thereafter, the processing returns to step S42.

The movement analysis device 2 configured as described above includes the sensor information acquisition unit 51 and the swing identification processing unit 52. The sensor information acquisition unit 51 acquires the sensor information that is the movement information from the sensor unit 1 which senses a series of movements performed by a target person. The swing identification processing unit 52 identifies the time of the start of the movement and the time of the completion based on the movement information acquired from the sensor information acquisition unit 51 and a predetermined threshold value. Based on the time of the start of the movement and the time of the completion that are identified, the swing identification processing unit 52 identifies a movement within the range of the operation. In this way, in the movement analysis device 2, the range of the movement of the swing can be identified easily and highly accurately.

The swing identification processing unit 52 determines whether or not the range of the time between the time of the start and the time of the completion that are identified is valid. In this way, in the movement analysis device 2, the range of the movement of the swing can be identified easily and highly accurately.

The sensor information that is the movement information includes, as the amount of movement, information on the angular velocity or the acceleration. When in the range of the time between the time of the start and the time of the completion that are identified, the number of times the angular velocity or the acceleration exceeds a predetermined threshold value exceeds a predetermined number of times, the swing identification processing unit 52 determines that the range of the time is valid. In this way, in the movement analysis device 2, with the angular velocity or the acceleration, the range of the movement of the swing can be identified easily and highly accurately.

The series of movements performed by the target person include a specific posture. When the specific posture is included in the range of the time in the movement information, the swing identification processing unit 52 determines that the range of the time is valid. In this way, in the movement analysis device 2, the range of the movement of the swing can be identified easily and highly accurately.

When the time of the maximum value or the minimum value of the amount of movement is included in the range of the time in the movement information, the swing identification processing unit 52 determines that the range of the time is valid. In this way, in the movement analysis device 2, the range of the movement of the swing can be identified easily and highly accurately.

When the time that elapses after the time of the start of the movement until the time of the completion exceeds a predetermined length, the swing identification processing unit 52 determines that the range of the time is invalid. In this way, in the movement analysis device 2, it is possible to determine that the probability of being the specific movement is low.

The sensor information acquisition unit 51 acquires the sensor information that is the movement, information in real time each time sensing is performed by the sensor unit 1. When the sensor information that is the movement information is acquired by the sensor information acquisition unit 51, the swing identification processing unit 52 identifies the time of the start of the movement and the time of the completion. In this way, in the movement analysis device 2, the movement can be identified in real time.

The movement analysis device 2 further includes the communication unit 20-2 which transmits, to an external device, the sensor information that is the movement information in a range including the time of the start of the series of movements and the time of the completion that are identified by the swing identification processing unit 52. In this way, in the movement analysis device 2, the amount of data related to storage and transmission can be reduced.

The swing identification processing unit 52 can change the timing of the start of the movement of the target person, and changes, to the time of the start of the movement, a timing earlier than the identified timing of the start of the movement. In this way, in the movement analysis device 2, the address can be identified.

The movement of the target person is the swing movement which includes at least the downswing. The swing identification processing unit 52 identifies the timing of the downswing of the target person based on the movement information and a predetermined threshold value, and when the downswing is identified, a timing at which a predetermined time has elapsed since the timing when the downswing is identified is identified as the time of the completion of the movement of the target person. In this way, in the movement analysis device 2, the downswing can be identified.

When the timing of the start of the movement of the target person is identified, and the timing of the downswing by the target person is not identified, the swing identification processing unit 52 stops processing related to the identification. In this way, in the movement analysis device 2, when the downswing is not identified, the processing can be stopped in the middle of the processing.

The predetermined threshold value includes a value that is set by the user or a value that is set based on the movement information sensed in the past. In this way, in the movement analysis device 2, an individual user setting can be reflected, or a value can be automatically set from the swing history.

The present invention is not limited to the embodiments described above, and as long as it is possible to achieve the object of the present invention, variations, modifications and the like are included in the present invention.

Although in the embodiments described above, the value of the threshold value D is determined by the noise data and the statistics of the actual swing, with consideration given to noise (after filter processing), sensor characteristics, and the tendency of the user, the value may be changed. The number of times of the intersection points with the threshold value D is also determined by the noise data and the statistics of the actual swing, and specifically, though in the present embodiment, 2 times is set to the specified value, since a larger number of times are detected when the downswing is detected earlier or when the movement of the finish is included, a range may be provided such that for example, the specified value is set within a range of 5 to 10 times. Since a swing without any intersection points is not present, at least one or more times may be set or with consideration given to significant variations in the swing, more than 10 times may be set. When a case where the downswing is detected earlier or a case where the movement of the finish is included can be detected, the number of times may be increased.

Although in the embodiments described above, the values of the threshold values (such as the intensity, the number of times and the time) are derived from statistical data so as to be specified, a configuration may be adopted in which the threshold values can be arbitrarily changed according to the tendency of the swing of the individual user.

Although in the embodiments described above, the values of the threshold values (such as the intensity, the number of times and the time) are derived from statistical data so as to be specified, a configuration may be adopted in which before the detection of the swing in the present embodiment, a marker is attached to the player, an image thereof is captured, image analysis is performed on the image and thus the threshold values are set according to data (movement rhythm and movement speed) obtained by the analysis of the movement of the swing. Here, as the method of the image analysis, a known, conventional, general technology is used.

Although in the embodiments described above, the values of the threshold values (such as the intensity, the number of times and the time) are derived from statistical data so as to be specified, a configuration may be adopted in which the threshold values can be arbitrarily changed according to the tendency of the swing of the individual user.

Although in the embodiments described above, the swing identification processing is performed in the movement analysis device 2, the swing identification processing may be performed in the sensor unit 1, an external server or the like.

Although in the embodiments described above, the sensor unit 1 is formed separately from the movement analysis device 2, the sensor unit 1 may be part of the movement analysis device 2.

Although in the embodiment described above, as an example of the movement analysis device 2 to which the present invention is applied, a smartphone is used, there is no particular limitation on this configuration. For example, the present invention can be applied to electronic devices in general which have the functions of swing identification processing. Specifically, for example, the present invention can be applied to a notebook type personal computer, a printer, a television set, a video camera, a portable navigation device, a mobile phone, a digital camera, a smart watch, a portable game device and the like.

The processing sequence described above can be executed by hardware, and can also be executed by software. In other words, the hardware configuration of FIG. 5 is merely an illustrative example, and the present invention is not particularly limited thereto. More specifically, the types of functional blocks employed to realize the above-described functions are not particularly limited to the examples shown in FIG. 5, so long as the movement analysis device 2 can be provided with the functions enabling the aforementioned processing sequence to be executed in its entirety. A single functional block may be configured by a single piece of hardware, a single installation of software, or a combination thereof. The functional configurations of the present embodiment are realized by a processor executing arithmetic processing, and processors that can be used for the present embodiment include a unit configured by a single unit of a variety of single processing devices such as a single processor, multi-processor, multi-core processor, etc., and a unit in which the variety of processing devices are combined with a processing circuit such as ASIC (Application Specific Integrated. Circuit) or FPGA (Field-Programmable Gate Array).

In the case of having the series of processing executed by software, the program constituting this software is installed from a network or recording medium to a computer or the like. The computer may be a computer equipped with dedicated hardware. In addition, the computer may be a computer capable of executing various functions, e.g., a general purpose personal computer, by installing various programs.

The storage medium containing such a program can not only be constituted by the removable medium 31-2 of FIG. 3 distributed separately from the device main body for supplying the program to a user, but also can be constituted by a storage medium or the like supplied to the user in a state incorporated in the device main body in advance. The removable medium 31 is composed of, for example, a magnetic disk (including a floppy disk), an optical disk, a magnetic optical disk, or the like. The optical disk is composed of, for example, a CD-ROM (Compact Disk-Read Only Memory), a DVD (Digital Versatile Disk), Blu-ray (Registered Trademark) or the like. The magnetic optical disk is composed of an MD (Mini-Disk) or the like. The storage medium supplied to the user in a state incorporated in the device main body in advance is constituted by, for example, the ROM 12-2 of FIG. 3 in which the program is recorded or a hard disk, etc. included in the storage unit. 19-2 of FIG. 3.

It should be noted that, in the present specification, the steps defining the program recorded in the storage medium include not only the processing executed in a time series following this order, but also processing executed in parallel or individually, which is not necessarily executed in a time series. In addition, in the present specification, the term 'system' shall mean a general device configured with a plurality of devices, a plurality of means, and the like.

The embodiments of the present invention described above are only illustrative, and are not to limit the technical scope of the present invention. The present invention can assume various other embodiments. Additionally, it is possible to make various modifications thereto such as omissions or replacements within a scope not departing from the spirit of the present invention. These embodiments or modifications thereof are within the scope and the spirit of the invention described in the present specification, and within the scope of the invention recited in the claims and equivalents thereof.

What is claimed is:

1. A movement analysis device comprising:
   a communication device via which movement information sensed at a predetermined time interval by a sensor device is acquired, the sensor device being attached to a target person and sensing a series of movements by the target person at the predetermined time interval during a period from before a start of the series of movements to completion of the series of movements; and
   a hardware processor configured to identify a plurality of states in the series of movements based on the movement information acquired from the sensor device and a plurality of threshold values,
   the plurality of threshold values including:
      a first threshold value set with respect to an intensity of the movement information;
      a second threshold value set with respect to a number of times that a predetermined situation occurs in the movement information; and
      a third threshold value set with respect to a continuous time period in the movement information.

2. The movement analysis device according to claim 1, wherein the identifying the plurality of states comprises:
   identifying a static state before the start of the series of movements;
   identifying a start of a first specific movement from among the series of movements, the first specific movement following the static state;
   identifying a candidate of a second specific movement from among the series of movements, the second specific movement being different from the first specific movement; and
   identifying whether the candidate corresponds to the another specific movement.

3. The movement analysis device according to claim 2, wherein the hardware processor identifies, as the static state, a state in which the intensity of the movement information is continuously lower than the first threshold value for a length of time equal to or greater than the third threshold value.

4. The movement analysis device according to claim 3, wherein the hardware processor identifies, as the start of the first specific movement, a timing at which the intensity of the movement information exceeds the first threshold value.

5. The movement analysis device according to claim 4, wherein the plurality of threshold values further include:
   a fourth threshold value set with respect to the intensity of the movement information, the fourth threshold value being higher than the first threshold value; and a fifth threshold value set with respect to a continuous time period in the movement information, the fifth threshold value being shorter than the third threshold value, and wherein the hardware processor identifies, as the completion of the series of movements, a state in which, at a timing following the static state, the intensity of the movement information is continuously lower than the fourth threshold value for a length of time equal to or greater than a fifth threshold value, and identifies a time period from the start of the first specific movement to the completion of the series of movements as the candidate of the second specific movement.

6. The movement analysis device according to claim 5, wherein the plurality of threshold values further include:

a sixth threshold value set with respect to the intensity of the movement information, the sixth threshold value being higher than the fourth threshold value;

a seventh threshold value set with respect to the intensity of the movement information, the seventh threshold value being higher than the sixth threshold value; and an eighth threshold value set with respect to a continuous time period in the movement information, the eighth threshold value being longer than a combination of the third threshold value and the fifth threshold value, and wherein the hardware processor identifies that the candidate corresponds to the second specific movement in a case in which (i) the movement information exceeds the seventh threshold value after having intersected with the sixth threshold value a number of times equal to or less than the second threshold value, and (ii) the time period that is identified as the candidate of the second specific movement falls within the eighth threshold value.

7. The movement analysis device according to claim 1, wherein the series of movements comprise movements included in a golf swing.

8. The movement analysis device according to claim 3, wherein the first specific movement is a golf backswing, and the second specific movement is a golf downswing.

9. The movement analysis device according to claim 1, wherein each of the first threshold value, the second threshold value, and the third threshold value is one of (i) a value set by a user and (ii) a value set based on previously acquired movement information.

10. A movement analysis method executed by a movement analysis device, the method comprising:

acquiring movement information sensed at a predetermined time interval from a sensor device, the sensor device being attached to a target person and sensing a series of movements by the target person at the predetermined time interval during a period from before a start of the series of movements to completion of the series of movements; and identifying a plurality of states in the series of movements based on the movement information acquired from the sensor device and a plurality of threshold values, the plurality of threshold values including:
a first threshold value set with respect to an intensity of the movement information;
a second threshold value set with respect to a number of times that a predetermined situation occurs in the movement information; and
a third threshold value set with respect to a continuous time period in the movement information.

11. A non-transitory computer-readable recording medium having a program stored thereon for controlling a computer included in a movement analysis device to execute processes comprising:

acquiring movement information sensed at a predetermined time interval from a sensor device, the sensor device being attached to a target person and sensing a series of movements by the target person at the predetermined time interval during a period from before a start of the series of movements to completion of the series of movements; and identifying a plurality of states in the series of movements based on the movement information acquired from the sensor device and a plurality of threshold values, the plurality of threshold values including:
a first threshold value set with respect to an intensity of the movement information;
a second threshold value set with respect to a number of times that a predetermined situation occurs in the movement information; and
a third threshold value set with respect to a continuous time period in the movement information.

* * * * *

UNITED STATES PATENT AND TRADEMARK OFFICE
CERTIFICATE OF CORRECTION

PATENT NO. : 10,661,142 B2
APPLICATION NO. : 15/813541
DATED : May 26, 2020
INVENTOR(S) : Shogo Hashimoto et al.

It is certified that error appears in the above-identified patent and that said Letters Patent is hereby corrected as shown below:

In the Claims

Column 15, Line 37 (Claim 8, Line 1), delete "claim 3," and insert --claim 2,--.

Signed and Sealed this
Twentieth Day of October, 2020

Andrei Iancu
*Director of the United States Patent and Trademark Office*